(12) United States Patent
Mizukura et al.

(10) Patent No.: US 10,992,917 B2
(45) Date of Patent: Apr. 27, 2021

(54) IMAGE PROCESSING DEVICE, IMAGE PROCESSING METHOD, PROGRAM, AND IMAGE PROCESSING SYSTEM THAT USE PARALLAX INFORMATION

(71) Applicant: SONY CORPORATION, Tokyo (JP)

(72) Inventors: Takami Mizukura, Kanagawa (JP); Koji Kashima, Kanagawa (JP); Kenji Takahasi, Kanagawa (JP); Hisakazu Shiraki, Kanagawa (JP); Daisuke Tsuru, Chiba (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/308,534

(22) PCT Filed: Apr. 21, 2017

(86) PCT No.: PCT/JP2017/016067
§ 371 (c)(1),
(2) Date: Dec. 10, 2018

(87) PCT Pub. No.: WO2017/217115
PCT Pub. Date: Dec. 21, 2017

(65) Prior Publication Data
US 2019/0158803 A1    May 23, 2019

(30) Foreign Application Priority Data
Jun. 17, 2016    (JP) .............................. JP2016-120888

(51) Int. Cl.
*H04N 13/128*    (2018.01)
*G02B 23/26*    (2006.01)
(Continued)

(52) U.S. Cl.
CPC ....... *H04N 13/128* (2018.05); *A61B 1/00009* (2013.01); *A61B 1/00193* (2013.01);
(Continued)

(58) Field of Classification Search
CPC ............. H04N 13/128; H04N 5/23264; H04N 5/23229; H04N 5/23212;
(Continued)

(56) References Cited

U.S. PATENT DOCUMENTS 5,625,408 A  *  4/1997 Matsugu .............. H04N 13/239
                                                    348/42
8,212,915 B1     7/2012 Clark et al.
(Continued)

FOREIGN PATENT DOCUMENTS

EP    2 629 504 A1    8/2013
JP    10-248807 A     9/1998
(Continued)

OTHER PUBLICATIONS

Extended Search Report issued in European Application 17813020.9—1124 dated Aug. 6, 2019.
(Continued)

*Primary Examiner* — William A Beutel
(74) *Attorney, Agent, or Firm* — Xsensus, LLP

(57) ABSTRACT

[Object] Observation is made possible by switching between a stereoscopic vision image and a depth-of-field extended image correspondingly to a situation.
[Solution] An image processing device according to the present disclosure, includes a photographing situation acquiring section that acquires information with regard to a photographing situation of an image for a left eye or an image for a right eye, and a determining section that determines correspondingly to the information with regard to the photographing situation whether to perform stereoscopic vision image processing for the image for a left eye or the image for a right eye, or whether to perform two-dimensional depth-of-field extension processing with at least one of the image for a left eye or the image for a right
(Continued)

eye. With this, it becomes possible to observe by switching between a stereoscopic vision image and a depth-of-field extended image correspondingly to a situation.

12 Claims, 10 Drawing Sheets

(51) Int. Cl.
    *G03B 15/00* (2021.01)
    *A61B 1/00* (2006.01)
    *G06T 5/50* (2006.01)
    *H04N 5/232* (2006.01)
    *H04N 13/00* (2018.01)

(52) U.S. Cl.
    CPC ............ *G02B 23/26* (2013.01); *G03B 15/00* (2013.01); *G06T 5/50* (2013.01); *H04N 5/23212* (2013.01); *H04N 5/23229* (2013.01); *H04N 5/23264* (2013.01); *H04N 2013/0081* (2013.01)

(58) Field of Classification Search
    CPC ........ H04N 2013/0081; A61B 1/00193; A61B 1/00009; G06T 5/50; G03B 15/00; G02B 23/26
    See application file for complete search history.

(56) References Cited

U.S. PATENT DOCUMENTS

| | | | |
|---|---|---|---|
| 8,937,646 B1 | 1/2015 | Baldwin | |
| 2011/0102558 A1* | 5/2011 | Moliton | H04N 13/128 348/54 |
| 2011/0304707 A1* | 12/2011 | Oyagi | G02B 27/225 348/51 |
| 2012/0093394 A1* | 4/2012 | Li | H04N 13/111 382/154 |
| 2012/0147197 A1* | 6/2012 | Hjelmstrom | H04N 5/23212 348/187 |
| 2013/0041216 A1* | 2/2013 | McDowall | G02B 5/04 600/109 |
| 2013/0208088 A1* | 8/2013 | Ishii | G03B 35/00 348/43 |
| 2014/0205061 A1* | 7/2014 | Sakaguchi | A61B 6/486 378/41 |
| 2014/0323801 A1* | 10/2014 | Konno | A61B 1/00009 600/103 |

FOREIGN PATENT DOCUMENTS

| | | |
|---|---|---|
| JP | 2011-143309 A | 7/2011 |
| JP | 2013-128723 A | 7/2013 |
| WO | 2013/141404 A1 | 9/2013 |

OTHER PUBLICATIONS

International Search Report dated Jul. 25, 2017 in PCT/JP2017/016067.

* cited by examiner

IMAGE PROCESSING DEVICE, IMAGE PROCESSING METHOD, PROGRAM, AND IMAGE PROCESSING SYSTEM THAT USE PARALLAX INFORMATION

TECHNICAL FIELD

The present disclosure relates to an image processing device, an image processing method, a program, and an image processing system.

BACKGROUND ART

Hitherto, for example, Patent Literature 1 described in the below describes providing an endoscope device that can switch a two-dimensional/three-dimensional observation state selectively, can obtain a high resolution and bright observation image of a body part to be inspected at the time of the two-dimensional observation, and can obtain a three-dimensional observation image as required.

CITATION LIST

Patent Literature

Patent Literature 1: JP H10-248807A

DISCLOSURE OF INVENTION

Technical Problem

When observing using a stereoscopic vision camera, depending on a scene, there is a case of wanting to observe a clear image being in-focus from the front up to the back than a stereoscopic vision observation. However, with the technology described in the above-described Patent Literature 1, although a body part to be inspected can be observed with high resolution, a clear image being in-focus from the front up to the back cannot be obtained.

Then, it has been desired to make it possible to observe by switching a stereoscopic vision image and a depth-of-field extended image in accordance with a situation.

Solution to Problem

According to the present disclosure, there is provided an image processing device, including: a photographing situation acquiring section that acquires information with regard to a photographing situation of an image for a left eye or an image for a right eye; and a determining section that determines correspondingly to the information with regard to the photographing situation whether to perform stereoscopic vision image processing for the image for a left eye or the image for a right eye, or whether to perform two-dimensional depth-of-field extension processing with at least one of the image for a left eye or the image for a right eye.

In addition, according to the present disclosure, there is provided an image processing method, including: acquiring information with regard to a photographing situation of an image for a left eye or an image for a right eye; and determining correspondingly to the information with regard to the photographing situation whether to perform stereoscopic vision image processing for the image for a left eye or the image for a right eye, or whether to perform two-dimensional depth-of-field extension processing with at least one of the image for a left eye or the image for a right eye.

In addition, according to the present disclosure, there is provided a program for causing a computer to function as: means for acquiring information with regard to a photographing situation of an image for a left eye or an image for a right eye; and means for determining correspondingly to the information with regard to the photographing situation whether to perform stereoscopic vision image processing for the image for a left eye or the image for a right eye, or whether to perform two-dimensional depth-of-field extension processing with at least one of the image for a left eye or the image for a right eye.

In addition, according to the present disclosure, there is provided an imaging system, including: an imaging device that images an image for a left eye and an image for a right eye; and an image processing device that includes an acquiring section that acquires information with regard to a photographing situation of an image for a left eye or an image for a right eye and a determining section that determines correspondingly to the information with regard to the photographing situation whether to perform stereoscopic vision image processing for the image for a left eye or the image for a right eye, or whether to perform two-dimensional depth-of-field extension processing with at least one of the image for a left eye or the image for a right eye.

In addition, according to the present disclosure, there is provided an image processing device, including: a captured image acquiring section that acquires an image for a left eye and an image for a right eye; and a depth-of-field extension processing section that extends a depth-of-field of each of the image for a left eye and the image for a right eye and creates a depth-of-field extended image by synthesizing the image for a left eye and the image for a right eye in each of which the depth-of-field has been extended.

In addition, according to the present disclosure, there is provided an image processing method, including: acquiring an image for a left eye and an image for a right eye; and extending a depth-of-field of each of the image for a left eye and the image for a right eye and creating a depth-of-field extended image by synthesizing the image for a left eye and the image for a right eye in each of which the depth-of-field has been extended.

In addition, according to the present disclosure, there is provided a program for causing a computer to function as: acquiring an image for a left eye and an image for a right eye; and extending a depth-of-field of each of the image for a left eye and the image for a right eye and creating a depth-of-field extended image by synthesizing the image for a left eye and the image for a right eye in each of which the depth-of-field has been extended.

Advantageous Effects of Invention

As described in the above, according to the present disclosure, it becomes possible to observe by switching a stereoscopic vision image and a depth-of-field extended image in accordance with a situation.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
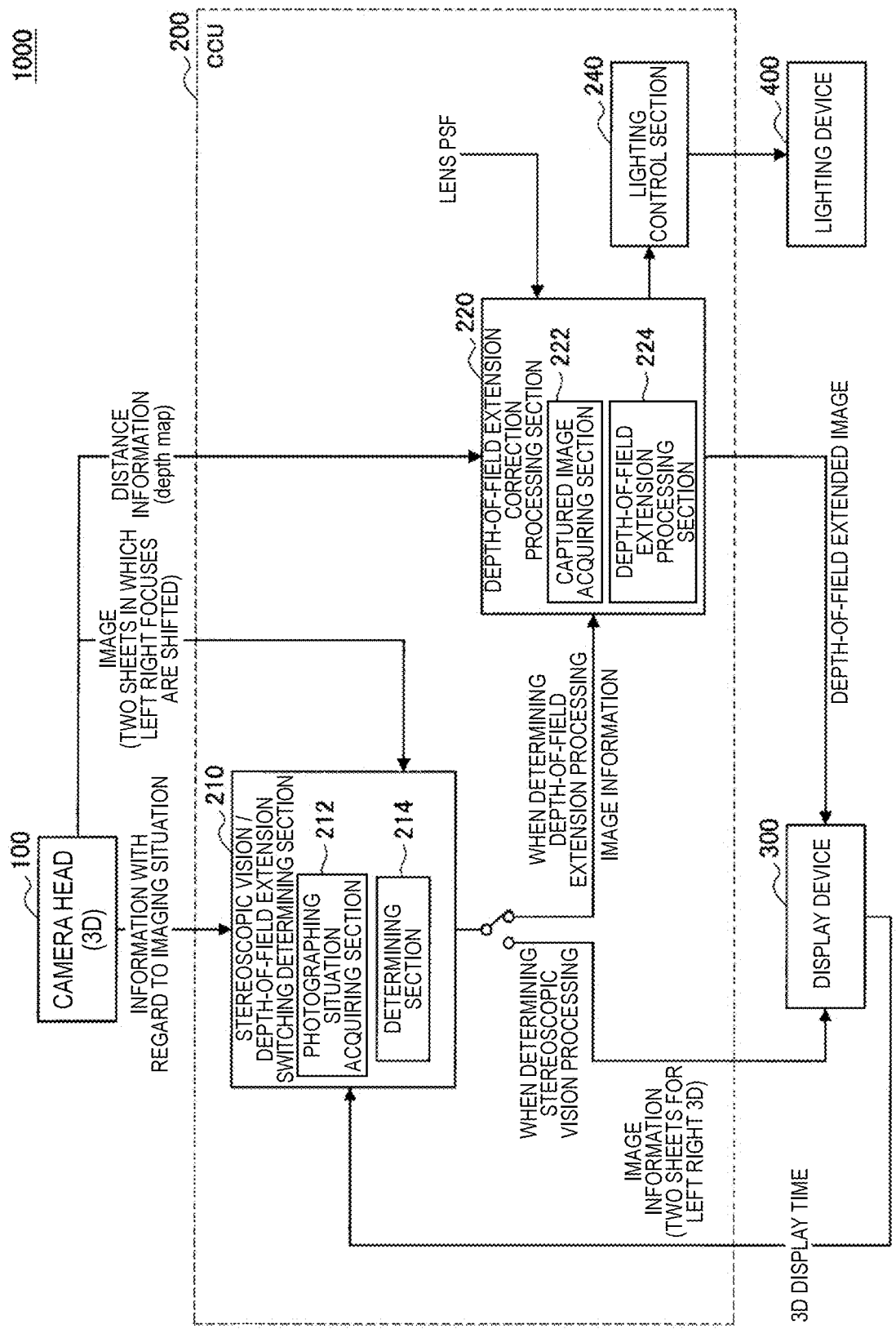
FIG. 1 is a schematic diagram showing a constitution of a system according to one embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

It should be noted that the description is given in the following order.

1.) Constitution Example of System
2.) Switching Between Stereoscopic Vision Image And EDoF Image
3.) Processing in Depth-of-Field Extension Correction Processing Section
3.1.) Basic processing in depth-of-field Extension Correction Processing Section
3.2.) Preparation of Two Sheets of Images
3.2.1.1.) Deconvolution (Deconvolution Integral, Deconvolution: Deconvolution) by Depth+PSF Data
3.2.1.2.) Using of Axial Chromatic Aberration Between R/G/B Channels
3.2.1.3.) Shifting of In-focus Position with Time Difference in Frame Sequential (FS)
3.2.2.) Processing for Performing EDoF with Each of Left and Right Images
3.3.) Alignment
3.4.) Synthesizing of Two Sheets Of Images (Creation of One Sheet of Depth-of-Field Extended Image)
3.4.1.) Synthesizing by Using Depth Map (Depth Map)
3.4.2.) Synthesizing by Using Defocus Map (Defocus Map)

1.) Constitution Example of System

First, with reference to FIG. 1, a constitution of a system 1000 according to one embodiment of the present disclosure is described. As shown in FIG. 1, this system 1000 includes a camera head (imaging device) 100, an image processing device 200, a display device 300, and a lighting device 400. The camera head 100 includes a stereoscopic vision camera having an image sensor and a zoom optical system and images a stereo image including one pair of left and right images (an image for a left eye and an image for a right eye). As one example, in the present embodiment, the camera head 200 is attached to an endoscope to be inserted in a body of a patient.

The image processing device 200 includes a stereoscopic vision / depth-of-field extension switching determining section 210, a depth-of-field extension correction processing section 220, and a lighting control section 240. In the present embodiment, image processing for stereoscopic vision and image processing for depth-of-field extension are exemplified especially. However, without being limited to that, a super resolution image may be created. The stereoscopic vision / depth-of-field extension switching determining section 210 includes a photographing situation acquiring section 212 that acquires information with regard to photographing situations, such as an optical zoom value, an electronic zoom value, operation information by a user, parallax information, and distance information, and a determining section 214 that determines correspondingly to information with regard to a photographing situation whether to output a three-dimensional stereoscopic vision image based on an image for a left eye and an image for a right eye or whether to output a two-dimensional depth-of-field extended image based on at least one of an image for a left eye or an image for a right eye. Moreover, the depth-of-field extension correction processing section 220 includes a captured image acquiring section 22 that acquires an image for a left eye and an image for a right eye, and a depth-of-field extension processing section 224 that extends a depth-of-field for each of an image for a left eye and an image for a right eye and creates a depth-of-field extended image by synthesizing an image for a left eye and an image for a right eye in each of which a depth-of-field has been extended.

The display device 300 includes a liquid crystal display (LCD) or the like, and displays an image having been subjected to image processing by the image processing section 200. The lighting device 400 illuminates a photographic subject to be imaged by the camera head 100.

2.) Switching between stereoscopic vision image and depth-of-field extended (EDoF: Extended Depth OF Field) image At the time of observing using a stereoscopic vision camera, there is a case where, depending on a scene, observing an extended depth-of-field (EDoF observation) is better than observing with a stereoscopic-vision (three dimensional) image. For example, in a stereoscopic vision image, in the case of performing extending by zoom, etc. so as to approach an object physically, resulting parallax is that extreme enough to cause asthenopia. Moreover, of continuing looking at a stereoscopic vision image over a long time may result in asthenopia. Furthermore, there may arise also a case of wanting to observe an EDoF image ofinstead of a stereoscopic vision image. In the present embodiment, in the case of meeting the conditions described in the below, stereoscopic vision indication is stopped and switched to depth-of-field extension (two dimensional) indication, thereby reducing these asthenopias.

For this reason, in the present embodiment, correspondingly to a situation at the time of photographing, an observer is enabled to observe by switching a stereoscopic vision image and a depth-of-field extended image (depth-of-field extended image) optimally. For example, cases, such as a case of observing through extending (a case where images are not fused), a case of observing sense time with depth (it is hard to see the front/back), and a case where asthenopia has occurred, are applied. In the case where a depth-of-field extended image is more suitable, a two-dimensional depth-of-field extended image (EDoF image) is synthesized from images imaged by the camera head 100, and is displayed. With this, it becomes possible to realize observation in which the depth-of-field is extended, while overcoming the above-described problem occurring in the case of observing with stereoscopic vision.

In more concrete terms, conditions for switching over from a stereoscopic vision image to a depth-of-field extended image, includes when extending, when determining a scene, when eyes have become tired, and so on, are set forth in detail below. The determining section 214 of the stereoscopic vision/depth-of-field extension switching determining section 210 of the image processing device 200 performs switching between a stereoscopic vision image and an EDoF image in accordance with the conditions discussed in detail below.

When Extending

In the case of having physically approached a photographic subject during observation with a stereoscopic vision image, parallax is increased so that a photographic subject jumps out too much to the front. For this reason, it becomes difficult for an observer to see an object, which leads to asthenopia. In such a case, by switching to a depth-of-field extended image, eyes are relieved and able to confirm image information. For this reason, the stereoscopic vision/depth-of-field extension switching determining section 210 of the image processing device 200 determines on the basis of parallax information and distance information whether or not to switch from a stereoscopic vision image to a depth-of-field extended image. Moreover, in the case of having extended by optical zoom during observation of a stereoscopic vision image, a focal length becomes short and a DoF depth-of-field becomes shallow. For this reason, the front and back of a focused photographic subject are blurred and becomes difficult to be seen. Moreover, in this case, parallax may become excessive by the extension. In such a case, in the case of having switched to an EDoF image, the front and back of a focused photographic subject can be observed clearly. For this reason, the stereoscopic vision/depth-of-field extension switching determining section 210 of the image processing device 200 determines on the basis of an optical zoom value and distance information whether or not to switch from a stereoscopic vision image to an EDoF image. Moreover, in the case of having extended by electronic zoom during observation of a stereoscopic vision image, a small blur that has not been bothersome at the time of bird's-eye view, becomes conspicuous, and it becomes difficult to identify an extended portion. Moreover, also in this case, parallax may become excessive. In such a case, in the case of having switched to an EDoF image, the extended portion, especially, information with regard to the background become well to be seen. For this reason, the stereoscopic vision/depth-of-field extension switching determining section 210 of the image processing device 200 determines on the basis of an electronic zoom value and distance information whether or not to switch from a stereoscopic vision image to an EDoF image.

When Determining Scene

In the case of observing a scene in which a photographic subject has depth in a stereoscopic vision image, the back side of the focused photographic subject becomes the outside of a depth-of-field and exceeds the image fusion limit. Accordingly, the photographic subject is blurred and may become not well to be seen. In such a case, in the case of having switched to an EDoF image, image information with regard to the back side becomes well to be seen. Accordingly, it becomes easier to grasp the whole, and it is possible to acquire partial detailed information than stereoscopic effect. For this reason, the stereoscopic vision/depth-of-field extension switching determining section 210 of the image processing device 200 determines on the basis of information with regard to a depth map whether or not to switch from a stereoscopic vision image to an EDoF image. Moreover, in the case of performing approach from different ports with a plurality of forcepses, a distance between a forceps attracting attention and the other forceps often separates as compared with a case of performing approach from the same port. Accordingly, a part of the working area becomes the outside of a depth-of-field, so that an image is blurred and may become not well to be seen. Also in such a case, in the case of having switched to an EDoF image, image information becomes well to be seen.

When Eyes Have Become Tired

After a fixed time has elapsed during observation of a stereoscopic vision image, where eyes may get tired or headache may occur. By switching to an EDoF image, eyes may be releivend. For this reason, the stereoscopic vision/depth-of-field extension switching determining section 210 determines on the basis of elapsed time information whether or not to switch from a stereoscopic vision image to an EDoF image.

When Designating by User

During observation with a stereoscopic vision image, there may be case of wanting to look detailed information with regard to the front and back of a focused photographic subject than grasping the positional relationship of the photographic subject with a stereoscopic effect in stereoscopic vision. In such a case, in the case of having switched to an EDoF image, it is possible to eliminate blur at the front and back of the focused photographic subject and to grasp detailed image information. For this reason, the stereoscopic vision/depth-of-field extension switching determining section 210 switches from a stereoscopic vision image to an EDoF image by making an operation of a user a trigger.

In this connection, it is possible to acquire a distance to an object from an image by utilizing parallax between right and left cameras, and as another technique, it is also possible to use a distance sensor, such as ToF (Time Of Flight). Moreover, as a technique of estimating distance information from an image, stereo matching has been well known.

A depth (jumping out, retracting) range for enjoying a stereoscopic image comfortably is referred to as a comfortable parallax range. According to the conventional research or the empirical rule, as a guide of the comfortable parallax range, a parallax angle is one degree (60 minutes) or less. Moreover, with regard to image fusion limit (a range in which double images are not caused), it is safe to consider that a parallax angle is about two degrees (120 minutes) or less. Although a parallax angle is defined as a difference between convergence angles, it is difficult to grasp intuitively. Instead, it is convenient to use a numerical value obtained by measuring parallax on a screen by the number of pixels, or a ratio relative to a screen width. A conversion table in the case of appreciating by a standard monitoring distance (three times the height of a screen) becomes as follows.

TABLE 1

In the case of a screen of 1920 × 1080

| Parallax angle | Parallax (number of pixels) | Parallax (ratio to screen width) |
| --- | --- | --- |
| 0.7 degrees (40 minutes) | 38 pixels | 1.9% |
| 1.0 degrees (60 minutes) | 57 pixels | 2.9% |
| 1.5 degrees (90 minutes) | 85 pixels | 4.4% |
| 2.0 degrees (120 minutes) | 113 pixels | 5.9% |

It is assumed that a parallax angle is θ and a distance to a monitor is L, parallax α (pixel) on a screen can be represented by α=L×tan(θ). It is assumed that L is 1080×3. From the above formula, in the case where the parallax angle is 1.0 degrees, it turns out that the parallax α (the number of pixels) becomes about 56.55 (pixels). In the case of having performed extending zoom, it becomes equivalent to a case where the distance L has been shortened. For example, in the case of two times zoom, it becomes 113 pixels at a parallax angle of 1.0 degree, and parallax becomes large.

As mentioned in the above, in the case where the parallax α is made extremely large, it has been known that asthenopia will be caused. A range in which image fusion through both eyes is performed naturally is referred to as a Nam's fusion area, and is defined such that parallax is about one degree or less to a screen surface serving as a standard. Moreover, as mentioned in the above, with regard to image fusion limit, it is safe to consider that a parallax angle is two degrees or less. For this reason, in the case where a parallax angle exceeds 2 degrees, the determining section 214 can determine to switch from a stereoscopic vision image to an EDoF image.

As shown in FIG. 1, from the camera head 100 to the image processing device 200, sent are various kinds of information with regard to photographing situations, such as an optical zoom value, an electronic zoom value, a user trigger (operation information by a user), parallax information, and distance information (depth map), besides a pair of left and right image information. The photographing situation acquiring section 212 of the stereoscopic vision/depth-of-field extension switching determining section 210 acquires these kinds of information with regard to the photographing situations, and the determining section 214 determines correspondingly to these kinds of information with regard to the photographing situation whether to output a three-dimensional stereoscopic vision image based on an image for a left eye and an image for a right eye or whether to output a two-dimensional depth-of-field extended image based on at least one of the image for a left eye or the image for a right eye. The stereoscopic vision/depth-of-field extension switching determining section 210 performs the switching between the stereoscopic vision image and the EDoF image as mentioned in the above on the basis of a result of the determination.

In the case of displaying the stereoscopic vision image as a result of the determination by the stereoscopic vision/depth-of-field extension switching determining section 210, one pair of left and right image information having been sent from the camera head 100 is sent to the display device 300, and the stereoscopic vision indication by one pair of left and right images is performed in the display device 300.

On the other hand, in the case of displaying the EDoF image as a result of the determination by the stereoscopic vision/depth-of-field extension switching determining section 210, one pair of left and right image information having been sent from the camera head 100 is sent to the depth-of-field extension correction processing section 220, and various kinds of processing for extending a depth-of-field is performed.

Figure 2:
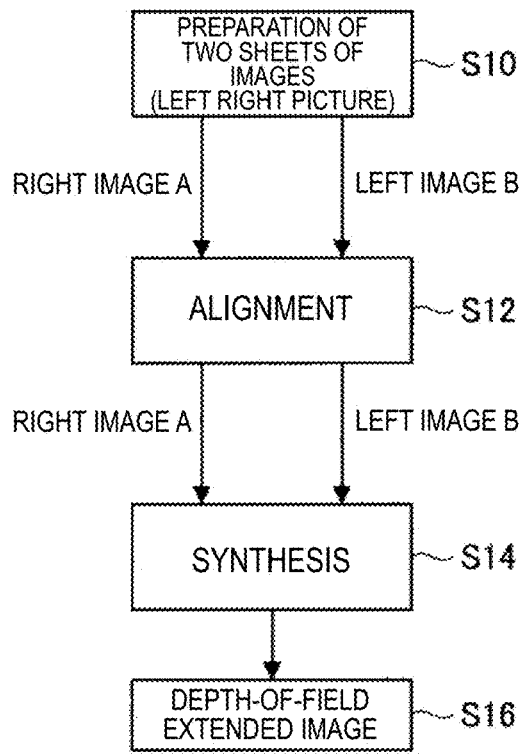
FIG. 2 is a schematic diagram showing a basic correction procedure in a depth-of-field extension correction processing section.

3.) Processing in Depth-of-Field Extension Correction Processing Section 3.1.) Basic Processing in Depth-of-Field Extension Correction Processing Section FIG. 2 is a schematic diagram showing a basic correction procedure in the depth-of-field extension correction processing section 220, and shows the processing performed mainly in the depth-of-field extension processing section 224. As a premise for performing the processing in FIG. 2, the captured image acquiring section 222 acquires one pair of left and right image information from the stereoscopic vision/depth-of-field extension switching determining section 210. First, in Step S10, an image for a right eye and an image for a left eye (a right image A and a left image B) of one pair of left and right having been sent from the stereoscopic vision/depth-of-field extension switching determining section 210 are prepared. These two sheets of images may be different in focusing position.

Moreover, in Step S10, EDoF processing (depth-of-field extension processing) is performed in each of left and right images. The details of the EDoF processing are mentioned later.

In the next step S12, alignment between the right image A and the left image B is performed. In concrete terms, a common portion between the right image A and the left image B is extracted, and shape correction is performing, thereby performing the alignment. At the time of performing the alignment, processing so as to cancel the parallax is performed.

In the next step S14, the right image A and the left image B having been subjected to the alignment are synthesized. At this time, depending on a depth position (depth position), a synthesis ratio between the right image A and the left image B is changed. With this, in the next step S16, a two-dimensional depth-of-field extended image is obtained.

Figure 3:
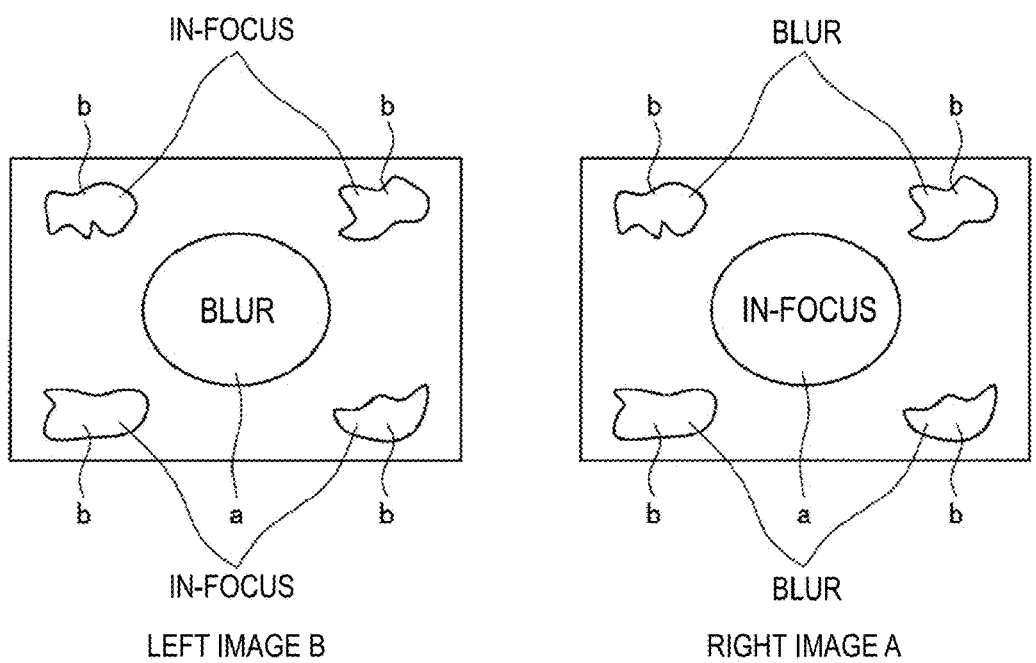
FIG. 3 is a schematic illustration showing a case of having acquired a right image A and a left image B that are different in focusing position, in Step S10 in FIG. 2.

FIG. 3 is a schematic illustration showing a case of having acquired a right image A and a left image B that are different in focusing position, in Step S10 of FIG. 2. As shown in FIG. 3, in the right image A, a photographic subject a at the center is in-focus, and a photographic subject b at the periphery (background) is blurred. On the other hand, in the right image B, a photographic subject a at the center is blurred, and a photographic subject b at the periphery is in-focus.

Figure 4:
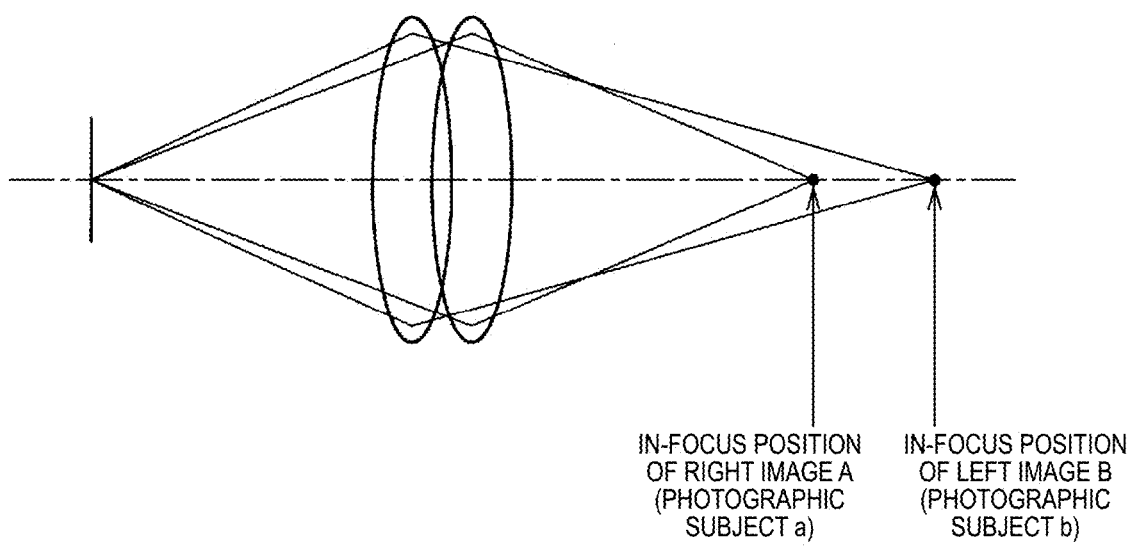
FIG. 4 is a schematic illustration showing the in-focus position of a right image A and the in-focus position of a left image B.

FIG. 4 is a schematic illustration showing the in-focus position of the right image A and the in-focus position of the left image B. As shown in FIG. 4, the right image A is in-focus at the position of the photographic subject a, and the left image B is in-focus at the position of the photographic subject b.

Figure 5:
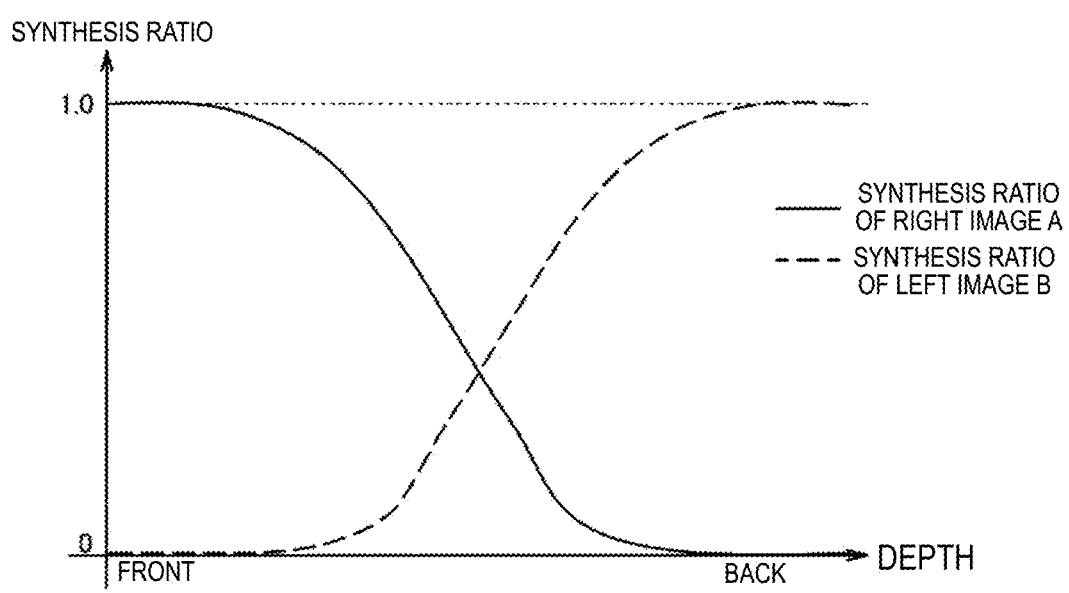
FIG. 5 is a characteristic diagram showing a synthesis ratio corresponding to a depth position.

After having performed the alignment in Step S12, in Step S14, the synthesis ratio between the right image A and the left image B is changed in accordance with a depth position. At the position of the photographic subject a at the center, the ratio of the right image A is made high, and at the photographic subject b at the periphery, the ratio of the left image B is made high. FIG. 5 is a characteristic diagram showing a synthesis ratio corresponding to a depth position. As a depth position becomes closer to the back (closer to the background), the ratio $R_A$ of the right image A becomes low, and the ratio $R_B$ of the left image B becomes large. Moreover, as a depth position becomes closer to the front, the ratio $R_A$ of the right image A becomes high, and the ratio $R_B$ of the left image B becomes low. In this connection, it is possible to set to $R_B=1-R_A$. A main image becomes the right image A that is in-focus at the center portion. On the basis of the depth map, by synthesizing the right image A and the left image B in accordance with FIG. 5, it becomes possible to change the synthesis ratio spatially, and it is possible to obtain a two-dimensional depth-of-field extended image that has been in-focus at both the center and the periphery.

Hereinafter, the preparation of two sheets of images in Step S10, the alignment in Step S12, and the synthesis of the two sheets of images in Step S16 in FIG. 2 are described in detail.

3.2.) Preparation of Two Sheets of Images 3.2.1.) Processing for Performing EDoF with Either Left or Right Image In the depth-of-field extension correction processing section 220, the EDoF processing can be performed independently for each of the right image A and the left image B. In this case, the EDoF is performed with only one sheet of an image for one eye of either left or right. In the EDoF processing using one sheet of an image for one eye, there are a plurality of variations shown in the below. In this case, since the EDoF is completed by only one eye, the preparation of two sheets of images different in in-focus position becomes a dummy. Accordingly, another one sheet of an image may be made a copy of an image having been subjected to the EDoF.

Figure 6:
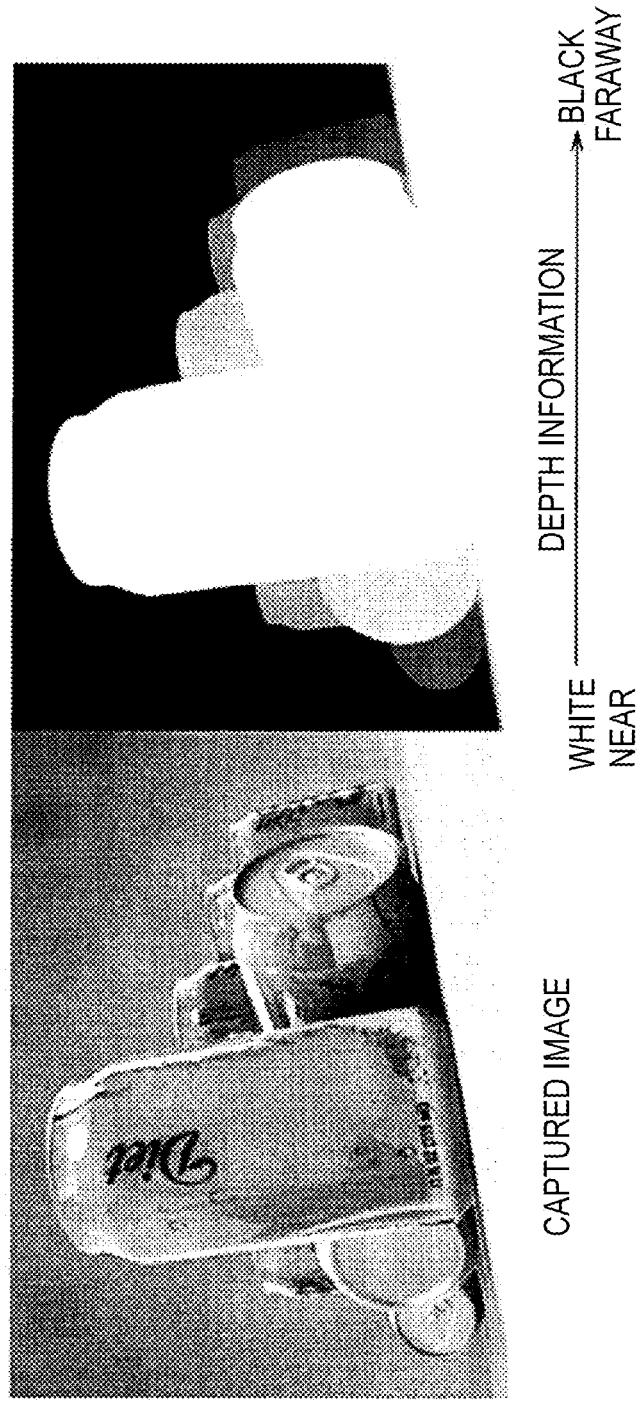
FIG. 6 is a schematic illustration showing spatial distance information (depth map).
Figure 7:
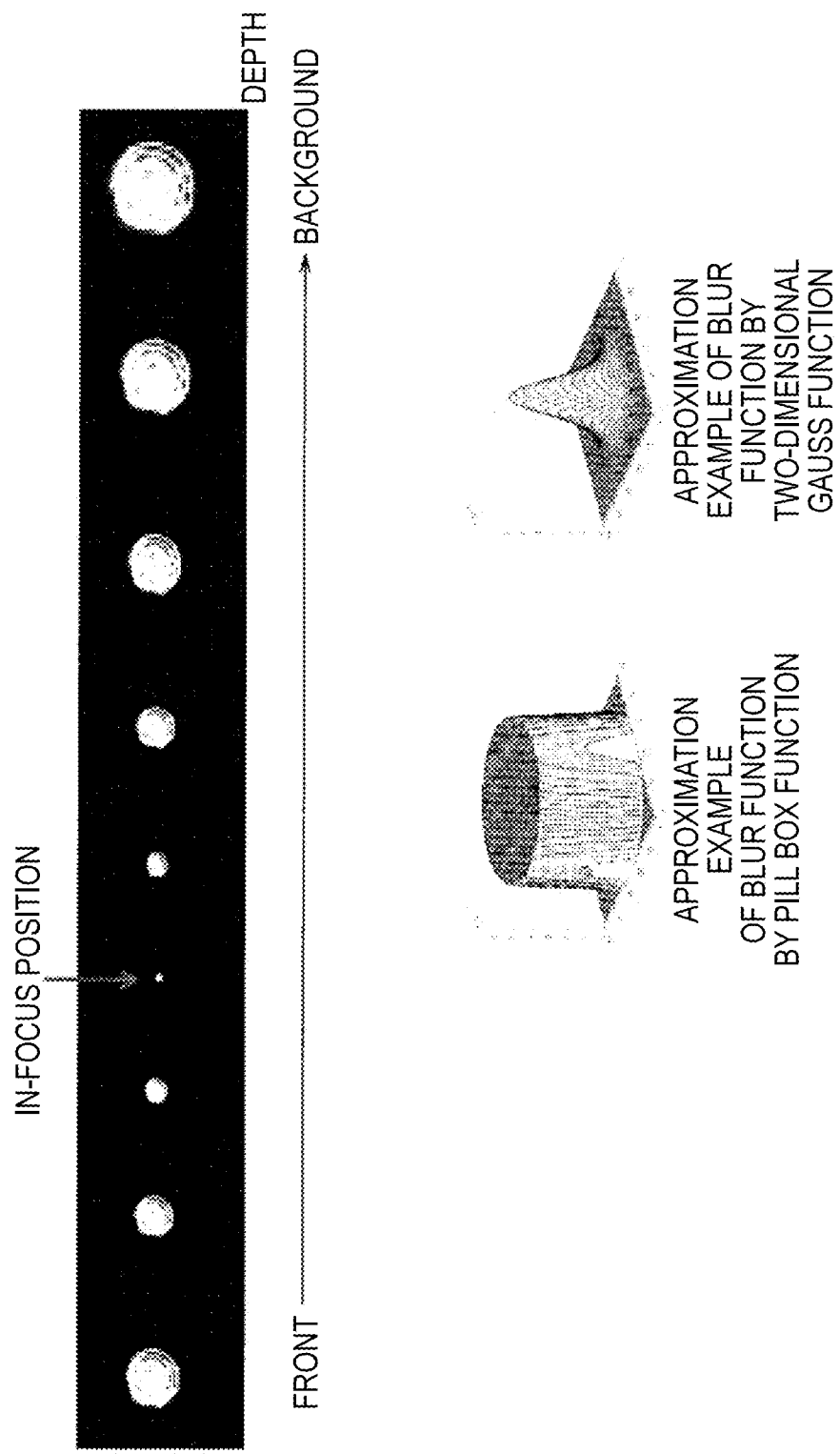
FIG. 7 is a schematic illustration showing the change characteristic, depending on a distance, of a PSF (Point Spread Function) showing how a lens blurs.

3.2.1.1.) Deconvolution (Deconvolution Integral, Deconvolution: Deconvolution) by Depth+PSF Data In this method, used are spatial distance information (depth map: depth map) as shown in FIG. 6 and the change characteristic, depending on a distance, of a PSF (Point Spread Function) showing how a lens blurs as shown in FIG. 7. In FIG. 6, a captured image is sown on the left side, and the depth information is shown on the right side. In the depth information on the right side, it is shown that as the density becomes close to black, a photographic subject is located far away (back), and as the density becomes close to white, a photographic subject is located near (front).

The depth information shown in FIG. 6 can be obtained from parallax information. As a result of block matching, the parallax information of left and right images can be obtained as the number of pixels, and the parallax information can be converted into distance information. Therefore, the depth information shown in FIG. 6 can be obtained with parallax information and distance information.

Moreover, FIG. 7 shows a situation that blur occurs correspondingly to a depth relative to an in-focus position, and as a distance from the in-focus position increases, blur becomes large. As shown in FIG. 7, the amount of blur according to a depth can be approximated with a blur function by Pill Box Function and a blur function by a two-dimensional Gauss function. The information with regard to the PSF shown in FIG. 7 has been acquired beforehand from the specification of the optical system of the camera head 100, and is input into the depth-of-field extension correction processing section 220. In this connection, the information with regard to the PSF may be acquired from the camera head 100.

The depth-of-field extension correction processing section 220 performs the EDoF processing on the basis of distance information and PSF information. At this time, the parallax information and the distance information may be calculated on the camera head 100 side, or may be calculated on the depth-of-field-extension-correction-processing-section 220 side. In the case where the information in FIG. 6 and FIG. 7 has been acquired, the amount of blur corresponding to a depth position can be known. Accordingly, by performing the reverse PSF filtering processing (deconvolution) to a blurred portion in a captured image, it is possible to obtain an EDoF image in which the blur has been removed.

3.2.1.2.) Using of Axial Chromatic Aberration Between R/G/B Channels

Correspondingly to the optical characteristics of a lens, there occurs a phenomenon (axial chromatic aberration) that an in-focus position becomes different depending on a difference in input wavelength light. For this reason, images of the respective channels of R, G, and B in a color image are different in in-focus position. By using these characteristics, as shown in FIG. 8 and FIG. 9, the high frequency component of each channel is synthesized (sharpness transfer) in other channels according to the depth (depth), whereby it is possible to obtain an EDoF image.

Figure 8:
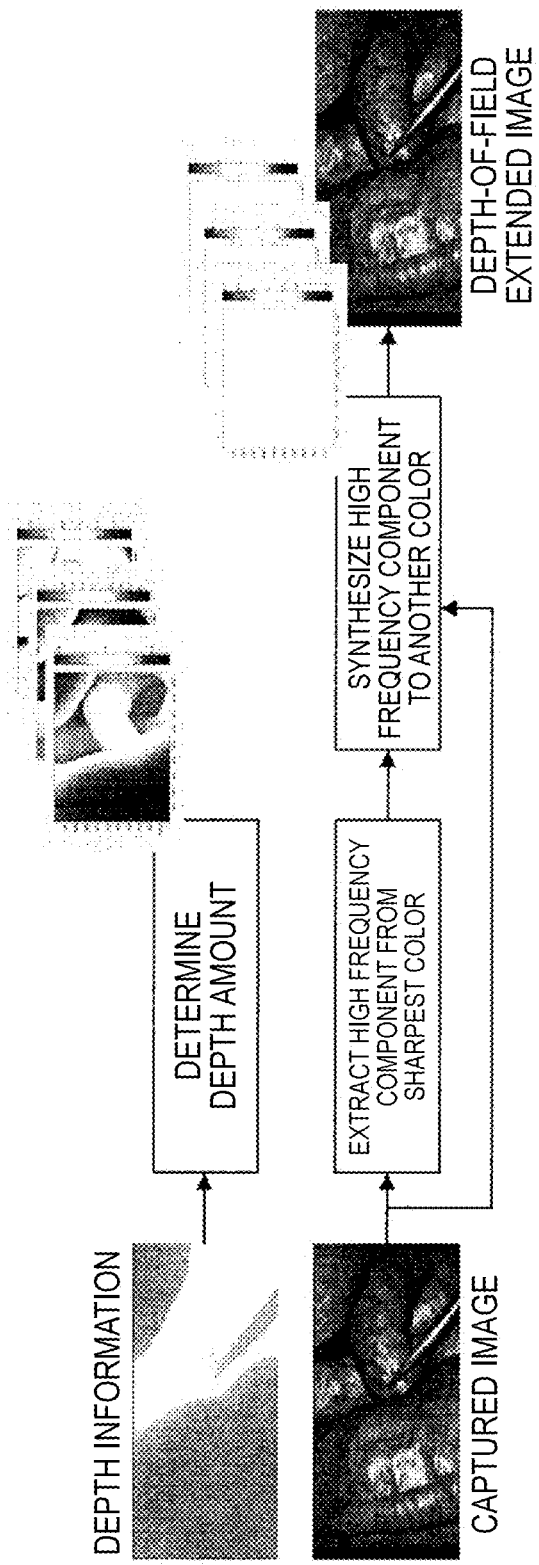
FIG. 8 is a schematic illustration showing an example in which axial chromatic aberration occurs due to a difference in input wavelength light correspondingly to the optical characteristics of a lens.
Figure 9:
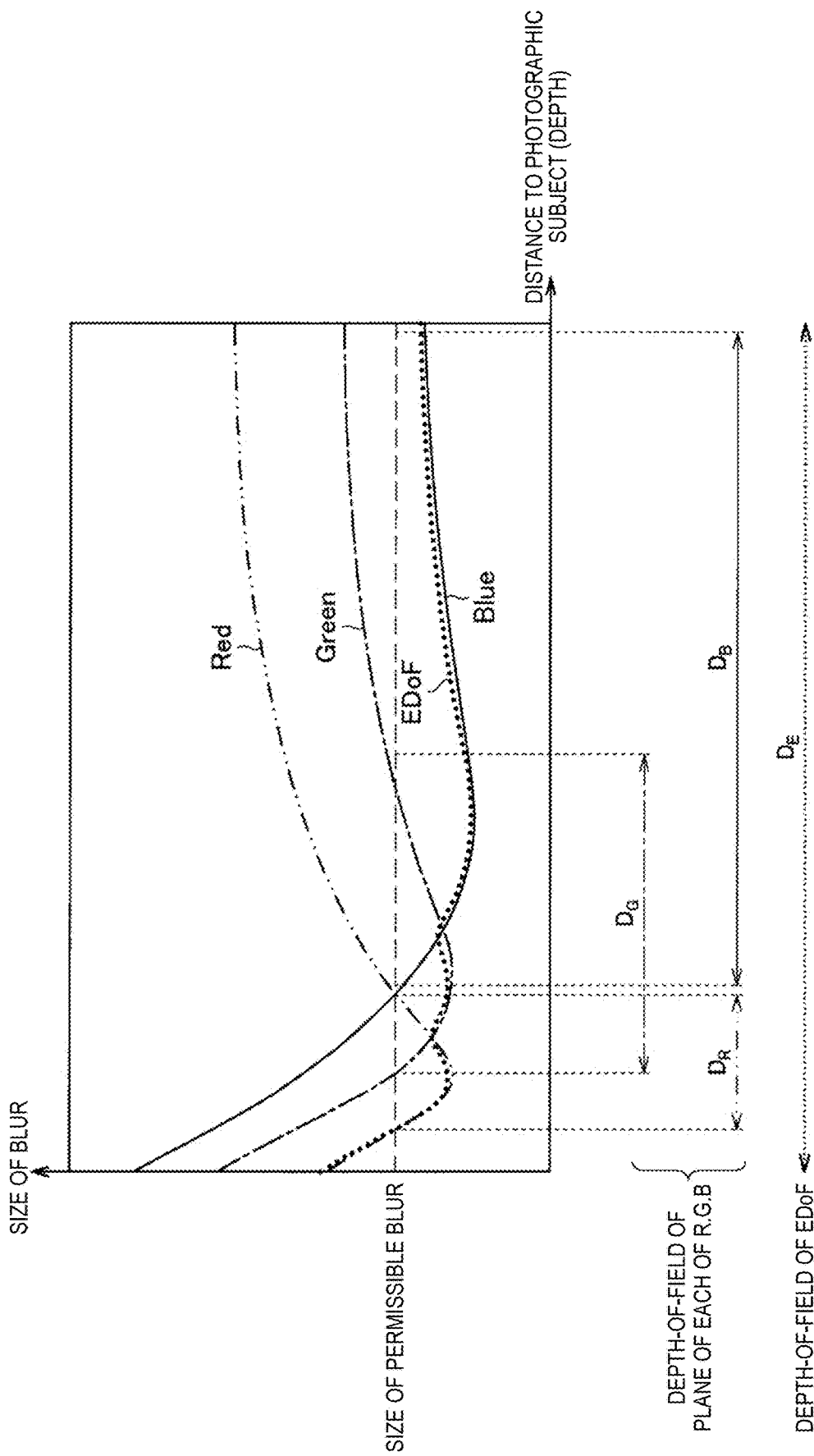
FIG. 9 is a schematic diagram showing an example of obtaining an EDoF image by synthesizing a high frequency component of each channel to other channel in accordance with a depth.

As shown in FIG. 8, the depth-of-field extension correction processing section 220 extracts a high frequency component from an image with the sharpest color. Moreover, the depth information as shown in FIG. 7 has been extracted separately. Then, the extracted high frequency component is synthesized in an image with the other color at the depth position of the image with the sharpest color. With this, as shown in FIG. 9, although the depth-of-fields of the images of the respective channels of R, G, and B are $D_R$, $D_G$, and $D_B$, respectively, by synthesizing the high frequency component of the sharpest channel according to the depth position, it is possible to extend the depth-of-field $D_E$ after having been subjected to the EDoF processing, greatly.

Figure 10:
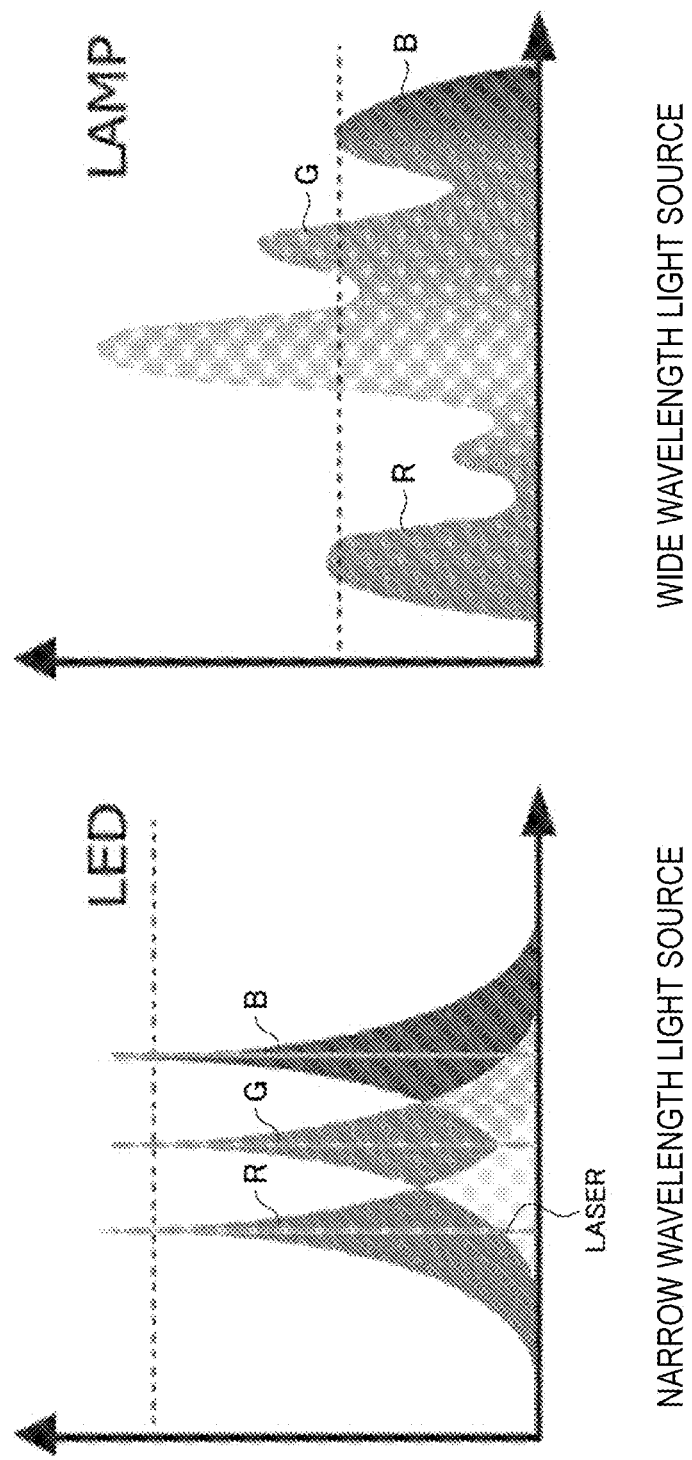
FIG. 10 is a schematic diagram showing an example of pulling out a difference in axial chromatic aberration between channels more by switching a light source interlockingly to one that has a wavelength peak and a narrow half width, such as RGB LED and Laser.

However, at the time of using this method, in the case of using a wide wavelength light source shown in the right diagram in FIG. 10, a mixing ratio of a wavelength signal component being in-focus and a wavelength signal component not being in-focus becomes high in the image information of the sharpest channel. Accordingly, the extraction degree of a high frequency component decreases, and even if synthesizing the high frequency component into the other channel, the effects of the depth-of-field extension may not be acquired sufficiently. In such a case, by switching to the lighting with a narrower band like LED or Laser shown in the left diagram in FIG. 10, it becomes possible to extract a signal component being in-focus so many. Accordingly, it is possible to enhance the effects of the depth-of-field extension. For this reason, the lighting control section 240 controls the lighting device 400 so as to perform irradiation to a photographic subject with a narrow wavelength light source or a wide wavelength light source as and shown in FIG. 10. In this way, by making a light source a narrow wavelength by interlocking the light source, it is also possible to cause axial chromatic aberration more and to raise the degree of EDoF. With this, it becomes possible to obtain an EDoF image with a wider depth-of-field.

3.2.1.3.) Shifting of In-focus Position with Time Difference in Frame Sequential (FS)

Figure 11:
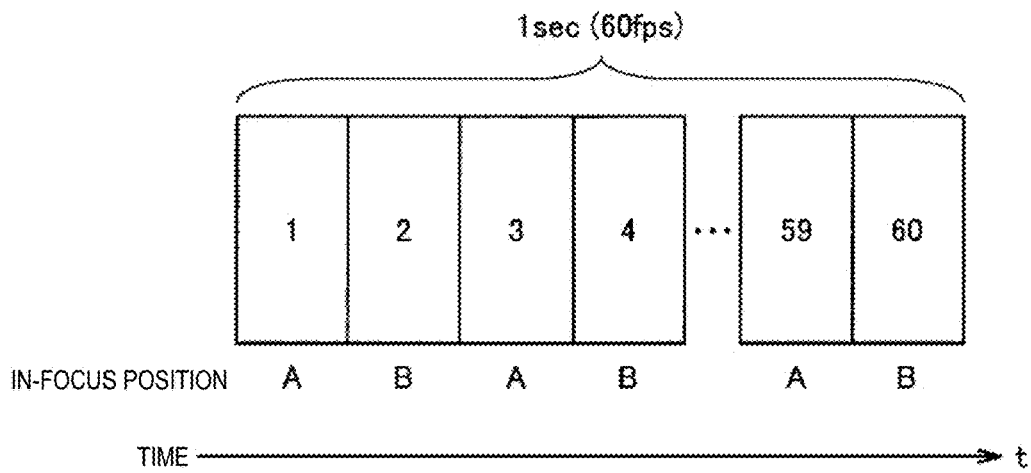
FIG. 11 is a schematic illustration showing an example of preparing two sheets of images having been photographed by shifting in-focus positions by photographing by shifting time around each frame so as to change an in-focus position.

Although a frame rate (Frame rate) becomes half, as shown in FIG. 11, in the case of photographing by changing in-focus positions A and B while shifting time for each frame, it becomes possible to prepare two sheets of images having been photographed by shifting the in-focus position. By synthesizing the two sheets of images, it is possible to obtain an EDoF image. As a synthesizing method, a method similar to that in FIG. 4 and FIG. 5 can be used. As one example, it is assumed that the in-focus position A is made the position of the photographic subject a in FIG. 4 and the in-focus position B is made the position of the photographic subject b in FIG. 4.

In this connection, in addition to the above-mentioned example, various well-known methods for performing the EDoF processing from one sheet of an image can be used. In the case where the depth information has been obtained, it is possible to perform the deconvolution corresponding to a distance to a photographic subject.

3.2.2.) Processing for Performing EDoF with Each of Left and Right Images

Figure 12:
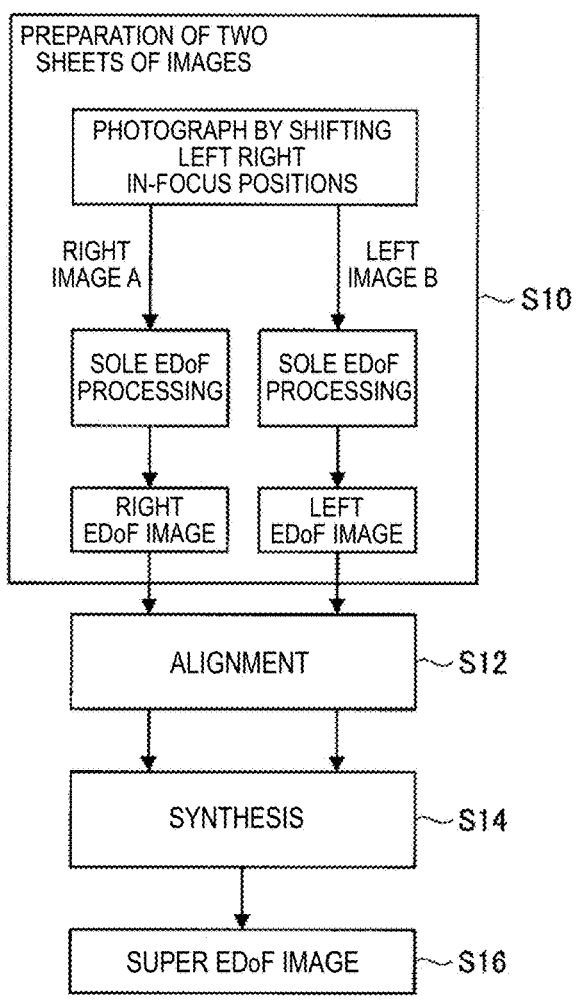
FIG. 12 is a schematic diagram showing an example of acquiring an EDoF image in which an in-focus position has been extended further than a case where an EDoF processing has been performed with an image for one eye alone, by synthesizing two kinds of EDoF images different in center in-focus position after having performed alignment.

In the case of performing the EDoF processing with an image for one eye alone, pan-focus (an image that is in-focus on the whole) cannot necessarily be created, and there is an effect that an in-focus range is extended from an original in-focus position to some extent. By performing photographing by shifting an in-focus position at the time of imaging by using left and right images, and by performing the above-described EDoF processing with each of images for the respective one eyes, it is possible to obtain two kinds of independent EDoF images different in center in-focus position. As shown in FIG. 12, by synthesizing these EDoF images after further performing alignment, it becomes possible to obtain an EDoF image (super EDoF image) in which the in-focus position has been extended more than a case where the EDoF processing has been performed with an image for one eye alone.

In an example shown in FIG. 12, the EDoF processing is performed independently for each of the left and right images with the above-mentioned technique. In FIG. 12, Steps S10 to S16 correspond to Steps S10 to S16 in FIG. 2. In Step S10 in FIG. 12, the right image A and the left image B are prepared by shifting the in-focus position of each of the left and right images, and the EDoF processing is performed independently for each of the right image A and the left image B, whereby the right EDoF image and the left EDoF image are obtained.

Subsequently, alignment is performed in Step S12, and the left and right images are synthesized in Step S14, whereby, in Step S16, it is possible to obtain a super EDoF image in which the depth-of-field has been extended more than that in FIG. 2. With this, it becomes possible to realize EDoF in which the depth is deeper than sole EDoF. In this connection, the details of Steps S12 to S16 are mentioned later.

As mentioned in the above, in addition to having made in-focus positions of the right image A and the left image B different, the EDoF processing has been performed independently for each of them, and thereafter, the both images are synthesized by the above-mentioned technique, whereby it becomes possible to extend the depth-of-field more.

3.3.) Alignment

Figure 13:
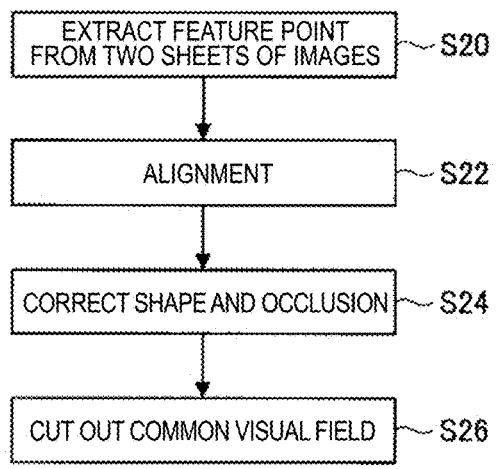
FIG. 13 is a flow chart showing alignment processing.
Figure 14:
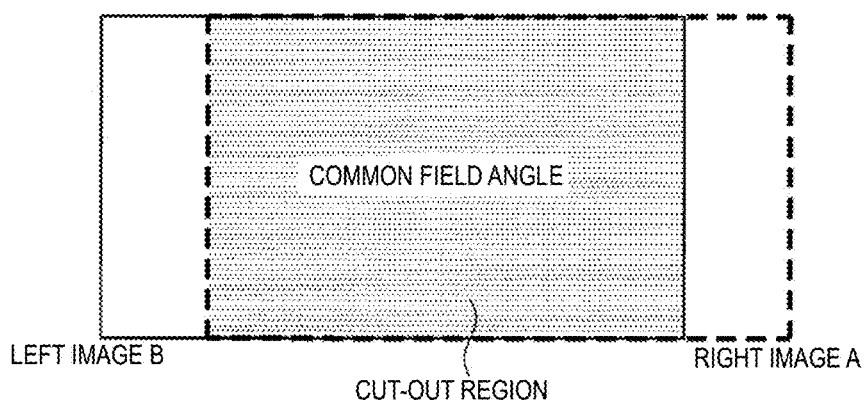
FIG. 14 is a schematic illustration showing an example of cutting out a common portion between left and right field angles and performing image processing to make a state such that a difference between left and right images becomes as small as possible except a difference in blur.

Since there exists parallax between left and right images, in the case of synthesizing them simply, a gap arises on the image. For this reason, processing for aligning the positions of two sheets of images and for cutting out a common field angle is performed, thereby performing alignment processing so as to cancel right-and-left parallax (Step S14 in FIG. 2 and FIG. 12). FIG. 13 is a flow chart showing alignment processing. First, in Step S20, a feature point that serves as an index of alignment, is extracted from the two sheets of images. In the next Step S22, alignment is performed by using the feature point. In here, a method of performing alignment by using an amount of feature, for example as described in JP 4136044B, can be used. In the case where several feature points becoming an index are extracted, in order to align their positions, in Step S24, by using a technique, for example, like affine transformation, left and right images are corrected by performing shape fitting while making them deform slightly. Moreover, in Step S24, as required, correction of occlusion, such as burying with peripheral pixels, is also executed. Subsequently, in Step S26, by cutting out a common portion between the left and right field angle as shown in FIG. 14, image processing is performed to make a state such that a difference between the left and right images becomes as small as possible except a difference in blur.

In this connection, in the case where the EDoF processing is performed with an image for one eye alone, since a copied image of the image having been subjected to the EDoF processing is enough as the other image, alignment is unnecessary.

3.4.) Synthesizing of Two Sheets of Images (Creation of One Sheet of Depth-of-Field Extended Image)

3.4.1.) Synthesizing by Using Depth Map (Depth Map)

In the case of having acquired a depth map, as shown in FIG. 5, a synthesis ratio of each of left and right images is determined correspondingly to a depth value, and a synthesis image is created by modulating the synthesis ratio for each of spatial pixels (pixel) of an image. In the case of an example in FIG. 5, in the vicinity of a central photographic subject, the image information of the right image A is almost used, and with regard to the background, the image information of the left image B is used. With regard to a photographic subject located at an intermediate distance, the synthesis ratio graph is referred such that the image information of each of the left image B and the right image A is synthesized moderately. The design of the transition portion of a synthesis ratio function may be performed on the basis of experience values, alternatively, the transition portion may be connected with a mathematically smooth curve, such as a sigmoid function so as not to cause rapid transition from the left image B to the right image A.

3.4.2.) Synthesizing by Using Defocus Map (Defocus Map)

Figure 15:
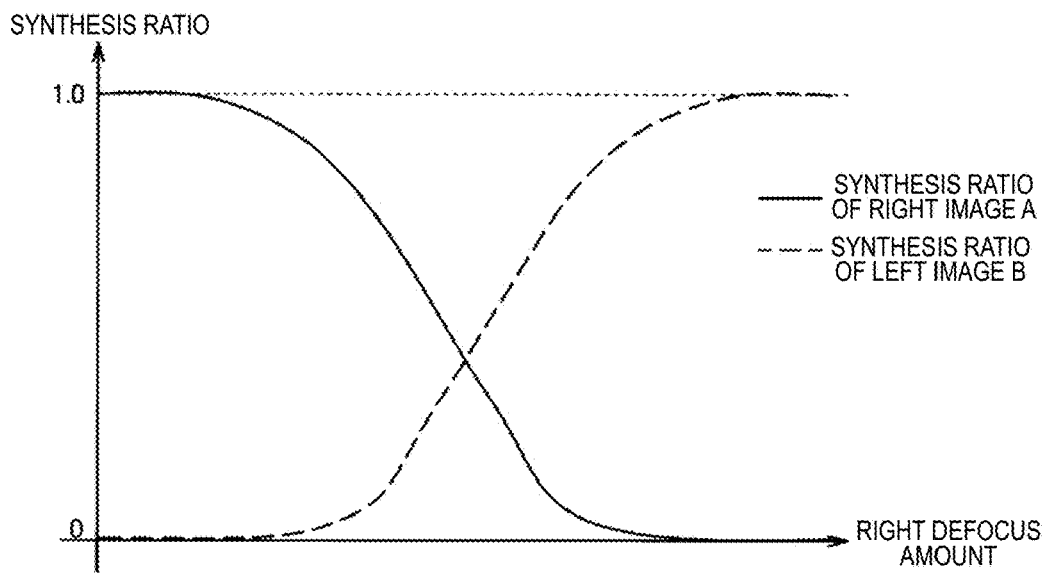
FIG. 15 is a characteristic diagram showing a synthesis ratio corresponding to an amount of defocus.

Even in the case where a depth map cannot be acquired, by estimating an amount of blur from an amount of feature of an image having been imaged, it is possible to synthesize images by making it an index. A well-known method is known that estimates a change of spatial blur from one of the left and right images and creates a defocus map. In the case where a defocus map has been created, with reference to it, the modulation as shown in FIG. 15 is executed. That is, on a place where an amount of defocus is small, a synthesis ratio of an image (in the example in FIG. 5, the right image A) having become a source of the defocus map, is raised, and, on a place not so, a synthesis ratio of the other one image is raised, whereby it is possible to acquire an image with many in-focus positions as a whole. In this connection, a difference between an amount of defocus and an amount of depth resides in the following point. That is, an amount of depth includes information with regard to whether to be front or back relative to an in-focus position. On the other hand, an amount of defocus does not include such information and includes only information showing an amount of a difference from the in-focus position. Since this method does not use a depth map, it is possible to suppress the calculation load for depth detection to the minimum, and there exists a merit that a distance sensor becomes unnecessary.

Besides the above, if the method synthesizes an image in which a depth-of-field is deeper, from a plurality of images, well-known techniques can be applied. For example, in the method for extending a depth-of-field by synthesizing from a plurality of images, without using a depth map or a defocus map explicitly, if there exist images, it is possible to create a synthetic image in which a focus is matched. The EDoF processing in the present embodiment is a concept including all the well-known methods of creating a depth-of-field extended image from a plurality of images.

As described in the above, according to the present embodiment, it is possible to perform observation with a three-dimensional stereoscopic vision image or observation with two-dimensional depth-of-field extended image correspondingly to a situation. Therefore, for example, in the case where asthenopia arises by observation of an obtained dimensional image, or in the case of wanting to obtain image information of a wide region from the front up to the back, it becomes possible to perform observation with a two-dimensional depth-of-field extended image correspondingly to a situation.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An image processing device, including:

a photographing situation acquiring section that acquires information with regard to a photographing situation of an image for a left eye or an image for a right eye; and a determining section that determines correspondingly to the information with regard to the photographing situation whether to perform stereoscopic vision image processing for the image for a left eye or the image for a right eye, or whether to perform two-dimensional depth-of-field extension processing with at least one of the image for a left eye or the image for a right eye.

(2)

The image processing device according to (1), in which the information with regard to the photographing situation is at least any of an optical zoom value when having imaged the image for a left eye or the image for a right eye, an electronic zoom value when having imaged the image for a left eye or the image for a right eye, parallax information with regard to the image for a left eye and the image for a right eye, distance information to a photographic subject of the image for a left eye or the image for a right eye, or operation information by a user.

(3)

The image processing device according to (1) or (2), further including:

a depth-of-field extension processing section, in which in a case where the determining section has determined to perform depth-of-field extension processing, the depth-of-field extension processing section creates a depth-of-field extended image by using at least one of the image for a left eye or the image for a right eye.

(4)

The image processing device according to (3), in which in a case where a parallax angle between the image for a left eye and the image for a right eye is two degrees or more, the depth-of-field extension processing section creates the depth-of-field extended image.

(5)

The image processing device according to (3), in which the depth-of-field extension processing section creates the depth-of-field extended image by performing inverse transformation for at least one of the image for a left eye or the image for a right eye on a basis of a blur function corresponding to a depth amount.

(6)

The image processing device according to (3), in which among respective images of R, G, and B colors, different in in-focus position, correspondingly to a depth position, the depth-of-field extension processing section synthesizes an image with most high-frequency components to an image of another color at a same depth position, thereby creating the depth-of-field extended image.

(7)

The image processing device according to (6), further including:

a lighting control section, in which the lighting control section controls illumination in order to adjust an in-focus position of each of the respective images of R, G, and B colors.

(8)

The image processing device according to (3), in which the depth-of-field extension processing section creates the depth-of-field extended image by synthesizing a plurality of images imaged at different in-focus positions for each frame.

(9)

The image processing device according to (3), in which the depth-of-field extension processing section extends a depth-of-field of each of the image for a left eye and the image for a right eye that have been imaged at different in-focus positions, and creates the depth-of-field extended image by synthesizing the image for a left eye and the image for a right eye in each of which the depth-of-field has been extended.

(10)

The image processing device according to (9), in which the depth-of-field extension processing section changes a synthesis ratio of each of the image for a left eye and the image for a right eye correspondingly to a depth position or a defocus position.

(11)

The image processing device according to (9), in which the depth-of-field extension processing section performs alignment between the image for a left eye and the image for a right eye, and performs the synthesizing.

(12)

The image processing device according to (9), in which the depth-of-field extension processing section cuts out a common range between the image for a left eye and the image for a right eye, and performs the synthesizing.

(13)
An image processing method, including:
acquiring information with regard to a photographing situation of an image for a left eye or an image for a right eye; and
determining correspondingly to the information with regard to the photographing situation whether to perform stereoscopic vision image processing for the image for a left eye or the image for a right eye, or whether to perform two-dimensional depth-of-field extension processing with at least one of the image for a left eye or the image for a right eye.

(14)
A program for causing a computer to function as:
means for acquiring information with regard to a photographing situation of an image for a left eye or an image for a right eye; and
means for determining correspondingly to the information with regard to the photographing situation whether to perform stereoscopic vision image processing for the image for a left eye or the image for a right eye, or whether to perform two-dimensional depth-of-field extension processing with at least one of the image for a left eye or the image for a right eye.

(15)
An imaging system, including:
an imaging device that images an image for a left eye and an image for a right eye; and
an image processing device that includes an acquiring section that acquires information with regard to a photographing situation of an image for a left eye or an image for a right eye and a determining section that determines correspondingly to the information with regard to the photographing situation whether to perform stereoscopic vision image processing for the image for a left eye or the image for a right eye, or whether to perform two-dimensional depth-of-field extension processing with at least one of the image for a left eye or the image for a right eye.

(16)
An image processing device, including:
a captured image acquiring section that acquires an image for a left eye and an image for a right eye; and
a depth-of-field extension processing section that extends a depth-of-field of each of the image for a left eye and the image for a right eye and creates a depth-of-field extended image by synthesizing the image for a left eye and the image for a right eye in each of which the depth-of-field has been extended.

(17)
The image processing device according to claim 16, in which the depth-of-field extension processing section changes a synthesis ratio of each of the image for a left eye and the image for a right eye correspondingly to a depth position or a defocus position.

(18)
The image processing device according to (16), in which the depth-of-field extension processing section performs alignment between the image for a left eye and the image for a right eye, cuts out a common range between the image for a left eye and the image for a right eye, and performs the synthesizing.

(19)
An image processing method, including:
acquiring an image for a left eye and an image for a right eye; and
extending a depth-of-field of each of the image for a left eye and the image for a right eye and creating a depth-of-field extended image by synthesizing the image for a left eye and the image for a right eye in each of which the depth-of-field has been extended.

(20)
A program for causing a computer to function as:
acquiring an image for a left eye and an image for a right eye; and
extending a depth-of-field of each of the image for a left eye and the image for a right eye and creating a depth-of-field extended image by synthesizing the image for a left eye and the image for a right eye in each of which the depth-of-field has been extended.

REFERENCE SIGNS LIST 100 camera head
200 image processing device
210 stereoscopic vision/depth-of-field extension switching determining section
212 photographing situation acquiring section
214 determining section
220 depth-of-field extension correction processing section
222 captured image acquiring section
224 depth-of-field extension processing section
240 lighting control section

The invention claimed is:

1. An image processing device, comprising:
circuitry configured to:
acquire an image for a left eye and an image for a right eye output by a medical imaging device;
generate parallax information based on the image for a left eye and the image for a right eye;
determine a parallax angle between the image for a left eye and the image for a right eye from the parallax information; and
on condition that the parallax angle between the image for a left eye and the image for a right eye is less than two degrees perform stereoscopic vision image processing for the image for a left eye and the image for a right eye; and
on condition that a parallax angle between the image for a left eve and the image for a right eye is equal to or greater than two degrees, perform two-dimensional depth-of-field extension processing with at least one of the image for a left eye or the image for a right eye,
wherein the two-dimensional depth-of-field extension is processed based on distance information between the medical imaging device and an object generated based on the parallax information.

2. The image processing device according to claim 1, wherein the circuitry is further configured to perform inverse transformation for at least one of the image for a left eye or the image for a right eye on a basis of a blur function corresponding to a depth amount.

3. The image processing device according to claim 1, wherein among respective images of R, G, and B colors, different in in-focus position, correspondingly to a depth position, the circuitry is further configured to synthesize an image with most high-frequency components to an image of another color at a same depth position, thereby creating a depth-of-field extended image.

4. The image processing device according to claim 3, wherein the circuitry is further configured to control illumination in order to adjust an in-focus position of each of the respective images of R, G, and B colors.

5. The image processing device according to claim 1, wherein the circuitry is further configured to create a depth-of-field extended image by synthesizing a plurality of images imaged at different in-focus positions for each frame.

6. The image processing device according to claim 1, wherein the circuitry is further configured to extend a depth-of-field of each of the image for a left eye and the image for a right eye that have been imaged at different in-focus positions, and create a depth-of-field extended image by synthesizing the image for a left eye and the image for a right eye in each of which the depth-of-field has been extended.

7. The image processing device according to claim 6, wherein the circuitry is further configured to change a synthesis ratio of each of the image for a left eye and the image for a right eye correspondingly to a depth position or a defocus position.

8. The image processing device according to claim 6, wherein circuitry is further configured to perform alignment between the image for a left eye and the image for a right eye, and synthesizing.

9. The image processing device according to claim 6, wherein the circuitry is further configured to cut out a common range between the image for a left eye and the image for a right eye, and perform synthesizing.

10. An image processing method, comprising:
acquiring an image for a left eye and an image for a right eye output by a medical imaging device;
generating parallax information based on the image for a left eye and the image for a right eye;
determining a parallax angle between the image for a left eye and the image for a right eye from the parallax information; and
responding to a first condition, wherein the parallax angle between the image for a left eye and the image for a right eye is less than two degrees, by performing stereoscopic vision image processing for the image for a left eye and the image for a right eye;
and responding to a second condition, wherein the parallax angle between the image for a left eye and the image for a right eye is equal to or greater than two degrees, by performing two-dimensional depth of field extension processing with at least one of the image for a left eye or the image for a right eye,
wherein the two-dimensional depth-of-field extension is processed based on distance information between the medical imaging device and an object generated based on the parallax information.

11. A non-transitory computer readable medium having stored thereon a program, that, when executed by a computer execute processing, the processing comprising:
acquiring an image for a left eye and an image for a right eye output by a. medical imaging device;
generating parallax information based on the image for a left eye and the image for a right eve;
determining a parallax angle between the image for a left eye and the image for a right eye from the parallax information; and
on condition that the parallax angle between the image for a left eye and the image for a right eye is less than two degrees,
performing stereoscopic vision image processing for the image for a left eve and the image for a right eye; and
on condition that the parallax angle between the image for a left eye and the image for a right eye is equal to or greater than two degrees, performing two-dimensional depth-of-field extension processing with at least one of the image for a left eye or the image for a right eye,
wherein the two-dimensional depth-of-field extension is processed based on distance information between the medical imaging device and an object generated based on the parallax information.

12. An imaging system, comprising:
an imaging device that images an image for a left eye and an image for a right eye; and
an image processing device that includes circuitry configured to:
acquire an image for a left eve and an image for a right eye,
generate parallax information based on the image for a left eye and the image for a right eye,
determine a parallax angle between the image for a left eye and the image for a right eve from the parallax information; and
on condition that the parallax angle between the image for a left eye and the image for a right eye is less than two degrees perform stereoscopic vision image processing for the image for a left eye and the image for a right eye; and
on condition that the parallax angle between the image for a left eye and the image for a right eye is equal to or greater than two degrees perform two-dimensional depth-of-field extension processing with at least one of the image for a left eye or the image for a right eye,
wherein the two-dimensional depth-of-field extension is processed based on distance information between the imaging device and an object generated based on the parallax information.

* * * * *